(12) United States Patent
Li et al.

(10) Patent No.: US 10,947,296 B2
(45) Date of Patent: *Mar. 16, 2021

(54) FUSION PROTEIN SLIT2D2(C386S)-HSA AND USE THEREOF IN TREATMENT OF FIBROTIC DISEASES

(71) Applicant: SUZHOU THINKING POWER BIOTECHNOLOGY CO., LTD., Suzhou (CN)

(72) Inventors: Huashun Li, Suzhou (CN); Baoyong Ren, Suzhou (CN); Peng Liu, Suzhou (CN)

(73) Assignee: SUZHOU THINKING POWER BIOTECHNOLOGY CO., LTD., Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/430,984

(22) Filed: Jun. 4, 2019

(65) Prior Publication Data

US 2019/0309050 A1 Oct. 10, 2019

Related U.S. Application Data

(63) Continuation of application No. PCT/CN2017/114599, filed on Dec. 5, 2017.

(30) Foreign Application Priority Data

Dec. 6, 2016 (CN) .......................... 2016 1 1110752

(51) Int. Cl.
| | |
|---|---|
| *C07K 14/765* | (2006.01) |
| *A61P 9/00* | (2006.01) |
| *A61K 9/08* | (2006.01) |
| *A61K 38/17* | (2006.01) |
| *C07K 14/47* | (2006.01) |
| *C12N 15/62* | (2006.01) |
| *C12N 15/85* | (2006.01) |
| *A61K 38/00* | (2006.01) |
| *A61P 11/16* | (2006.01) |
| *A61K 9/00* | (2006.01) |

(52) U.S. Cl.
CPC .......... *C07K 14/765* (2013.01); *A61K 9/0019* (2013.01); *A61K 9/08* (2013.01); *A61K 38/1709* (2013.01); *A61P 9/00* (2018.01); *A61P 11/16* (2018.01); *C07K 14/47* (2013.01); *C07K 14/4702* (2013.01); *C12N 15/62* (2013.01); *C12N 15/85* (2013.01); *A61K 38/00* (2013.01); *C07K 2319/31* (2013.01)

(58) Field of Classification Search
CPC .. A61K 38/00; A61K 38/1709; A61K 9/0019; A61K 9/08; A61K 9/19; A61P 11/16; A61P 9/00; C07K 14/47; C07K 14/4702; C07K 14/765; C07K 2319/31; C12N 15/62; C12N 15/85

See application file for complete search history.

(56) References Cited

U.S. PATENT DOCUMENTS

| | | | | |
|---|---|---|---|---|
| 10,336,813 | B2* | 7/2019 | Li | ...................... C07K 14/4702 |
| 2018/0094045 | A1* | 4/2018 | Li | ........................ C07K 14/765 |
| 2018/0163214 | A1* | 6/2018 | Li | .......................... A61K 47/50 |
| 2019/0309050 | A1* | 10/2019 | Li | ............................ A61K 9/08 |
| 2020/0087362 | A1* | 3/2020 | Li | ........................ C07K 14/765 |

FOREIGN PATENT DOCUMENTS

| | | |
|---|---|---|
| CU | 106543278 A | 3/2017 |
| WO | 2014194402 A1 | 12/2014 |
| WO | 2015168469 A1 | 11/2015 |
| WO | 2016179861 A1 | 11/2016 |

OTHER PUBLICATIONS

NIH Public Access Author Manuscript, Mar. 17, 2017, Targeting Robo4-Dependent Slit Signaling to Survive the Cytokine Storm in Sepsis.
International Search Report for International Application No. PCT/CN2017/114599, Nucleotide and/or amino acid sequence(s).
First Office Action for Application No. or Publication No. 201611110752.9, The State Intellectual Property Office of People's Republic of China.
Patent Cooperation Treaty, Written Opinion of the International Searching Authority, International Application No. PCT/CN2017/114599.

* cited by examiner

*Primary Examiner* — Marcela M Cordero Garcia
(74) *Attorney, Agent, or Firm* — Flener IP & Business Law; Zareefa B. Flener

(57) ABSTRACT

The present invention relates to the field of biomedical technology, in particular to a fusion protein Slit2D2 (C386S)-HSA and use thereof in the treatment and/or prevention of fibrotic diseases. In the fusion protein, the amino acid residue is mutated on the basis of the Slit2D2 domain, which improves the stability of the fusion protein compared with the native protein. The above fusion protein is obtained by fusing Slit2D2(C386S) with HSA protein, which prolongs the metabolism time of the drug while improving the stability of the drug. The fusion protein provided by the present invention is more effective than the positive control drug in the prevention and treatment of fibrotic diseases, particularly pulmonary fibrosis, and shows good drug-forming properties.

18 Claims, 8 Drawing Sheets

Specification includes a Sequence Listing.

A: normal; B: Score 1; C: Score 2; D: Score 3; E: Score 4; F: Score 5; G: Score 6; H: Score 7; I: Score 8

SEQUENCE LISTING

```
<160> NUMBER OF SEQ ID NOS: 4

<210> SEQ ID NO 1
<211> LENGTH: 209
<212> TYPE: PRT
<213> ORGANISM: Unknown
<220> FEATURE:
<223> OTHER INFORMATION: Slit2D2(C386S) protein

<400> SEQUENCE: 1

Leu His Cys Pro Ala Ala Cys Thr Cys Ser Asn Asn Ile Val Asp Cys
1               5                   10                  15

Arg Gly Lys Gly Leu Thr Glu Ile Pro Thr Asn Leu Pro Glu Thr Ile
            20                  25                  30

Thr Glu Ile Arg Leu Glu Gln Asn Thr Ile Lys Val Ile Pro Pro Gly
        35                  40                  45

Ala Phe Ser Pro Tyr Lys Lys Leu Arg Arg Ile Asp Leu Ser Asn Asn
    50                  55                  60

Gln Ile Ser Glu Leu Ala Pro Asp Ala Phe Gln Gly Leu Arg Ser Leu
65                  70                  75                  80

Asn Ser Leu Val Leu Tyr Gly Asn Lys Ile Thr Glu Leu Pro Lys Ser
                85                  90                  95

Leu Phe Glu Gly Leu Phe Ser Leu Gln Leu Leu Leu Leu Asn Ala Asn
            100                 105                 110

Lys Ile Asn Ser Leu Arg Val Asp Ala Phe Gln Asp Leu His Asn Leu
        115                 120                 125

Asn Leu Leu Ser Leu Tyr Asp Asn Lys Leu Gln Thr Ile Ala Lys Gly
    130                 135                 140

Thr Phe Ser Pro Leu Arg Ala Ile Gln Thr Met His Leu Ala Gln Asn
145                 150                 155                 160

Pro Phe Ile Cys Asp Cys His Leu Lys Trp Leu Ala Asp Tyr Leu His
                165                 170                 175

Thr Asn Pro Ile Glu Thr Ser Gly Ala Arg Cys Thr Ser Pro Arg Arg
            180                 185                 190

Leu Ala Asn Lys Arg Ile Gly Gln Ile Lys Ser Lys Lys Phe Arg Cys
        195                 200                 205

Ser

<210> SEQ ID NO 2
<211> LENGTH: 627
<212> TYPE: DNA
<213> ORGANISM: Unknown
<220> FEATURE:
<223> OTHER INFORMATION: Sequence encoding Slit2D2(C386S)

<400> SEQUENCE: 2
ttgcactgcc ctgccgcctg tacctgtagc aacaatatcg tagactgtcg tgggaaggt       60 ctcactgaga tccccacaaa tcttccagag accatcacag aaatacgttt ggaacagaac     120
acaatcaaag tcatccctcc tggagctttc tcaccatata aaaagcttag acgaattgac     180
ctgagcaata atcagatctc tgaacttgca ccagatgctt ccaaggact acgctctctg      240
```

-continued

```
aattcacttg tcctctatgg aaataaaatc acagaactcc ccaaaagttt atttgaagga    300
ctgttttcct tacagctcct attattgaat gccaacaaga taaacagtct tcgggtagat    360
gcttttcagg atctccacaa cttgaacctt ctctccctat atgacaacaa gcttcagacc    420
atcgccaagg ggacctttc acctcttcgg gccattcaaa ctatgcattt ggcccagaac     480 cccttattt gtgactgcca tctcaagtgg ctagcggatt atctccatac caacccgatt     540
gagaccagtg gtgcccgttg caccagcccc cgccgcctgg caaacaaaag aattggacag    600
atcaaaagca agaaattccg ttgttca                                        627
```

<210> SEQ ID NO 3
<211> LENGTH: 794
<212> TYPE: PRT
<213> ORGANISM: Unknown
<220> FEATURE:
<223> OTHER INFORMATION: Fusion protein Slit2D2(C386S)-HSA

<400> SEQUENCE: 3

```
Leu His Cys Pro Ala Ala Cys Thr Cys Ser Asn Asn Ile Val Asp Cys
1               5                   10                  15

Arg Gly Lys Gly Leu Thr Glu Ile Pro Thr Asn Leu Pro Glu Thr Ile
            20                  25                  30

Thr Glu Ile Arg Leu Glu Gln Asn Thr Ile Lys Val Ile Pro Pro Gly
        35                  40                  45

Ala Phe Ser Pro Tyr Lys Lys Leu Arg Arg Ile Asp Leu Ser Asn Asn
    50                  55                  60

Gln Ile Ser Glu Leu Ala Pro Asp Ala Phe Gln Gly Leu Arg Ser Leu
65                  70                  75                  80

Asn Ser Leu Val Leu Tyr Gly Asn Lys Ile Thr Glu Leu Pro Lys Ser
                85                  90                  95

Leu Phe Glu Gly Leu Phe Ser Leu Gln Leu Leu Leu Asn Ala Asn
            100                 105                 110

Lys Ile Asn Ser Leu Arg Val Asp Ala Phe Gln Asp Leu His Asn Leu
        115                 120                 125

Asn Leu Leu Ser Leu Tyr Asp Asn Lys Leu Gln Thr Ile Ala Lys Gly
    130                 135                 140

Thr Phe Ser Pro Leu Arg Ala Ile Gln Thr Met His Leu Ala Gln Asn
145                 150                 155                 160

Pro Phe Ile Cys Asp Cys His Leu Lys Trp Leu Ala Asp Tyr Leu His
                165                 170                 175

Thr Asn Pro Ile Glu Thr Ser Gly Ala Arg Cys Thr Ser Pro Arg Arg
            180                 185                 190

Leu Ala Asn Lys Arg Ile Gly Gln Ile Lys Ser Lys Lys Phe Arg Cys
        195                 200                 205

Ser Asp Ala His Lys Ser Glu Val Ala His Arg Phe Lys Asp Leu Gly
    210                 215                 220

Glu Glu Asn Phe Lys Ala Leu Val Leu Ile Ala Phe Ala Gln Tyr Leu
225                 230                 235                 240

Gln Gln Cys Pro Phe Glu Asp His Val Lys Leu Val Asn Glu Val Thr
                245                 250                 255

Glu Phe Ala Lys Thr Cys Val Ala Asp Glu Ser Ala Glu Asn Cys Asp
            260                 265                 270

Lys Ser Leu His Thr Leu Phe Gly Asp Lys Leu Cys Thr Val Ala Thr
        275                 280                 285

Leu Arg Glu Thr Tyr Gly Glu Met Ala Asp Cys Cys Ala Lys Gln Glu
```

```
            290                 295                 300
Pro Glu Arg Asn Glu Cys Phe Leu Gln His Lys Asp Asp Asn Pro Asn
305                 310                 315                 320

Leu Pro Arg Leu Val Arg Pro Glu Val Asp Val Met Cys Thr Ala Phe
                325                 330                 335

His Asp Asn Glu Glu Thr Phe Leu Lys Lys Tyr Leu Tyr Glu Ile Ala
            340                 345                 350

Arg Arg His Pro Tyr Phe Tyr Ala Pro Glu Leu Leu Phe Phe Ala Lys
                355                 360                 365

Arg Tyr Lys Ala Ala Phe Thr Glu Cys Cys Gln Ala Ala Asp Lys Ala
        370                 375                 380

Ala Cys Leu Leu Pro Lys Leu Asp Glu Leu Arg Asp Glu Gly Lys Ala
385                 390                 395                 400

Ser Ser Ala Lys Gln Arg Leu Lys Cys Ala Ser Leu Gln Lys Phe Gly
                405                 410                 415

Glu Arg Ala Phe Lys Ala Trp Ala Val Ala Arg Leu Ser Gln Arg Phe
            420                 425                 430

Pro Lys Ala Glu Phe Ala Glu Val Ser Lys Leu Val Thr Asp Leu Thr
                435                 440                 445

Lys Val His Thr Glu Cys Cys His Gly Asp Leu Leu Glu Cys Ala Asp
        450                 455                 460

Asp Arg Ala Asp Leu Ala Lys Tyr Ile Cys Glu Asn Gln Asp Ser Ile
465                 470                 475                 480

Ser Ser Lys Leu Lys Glu Cys Cys Glu Lys Pro Leu Leu Glu Lys Ser
                485                 490                 495

His Cys Ile Ala Glu Val Glu Asn Asp Glu Met Pro Ala Asp Leu Pro
            500                 505                 510

Ser Leu Ala Ala Asp Phe Val Glu Ser Lys Asp Val Cys Lys Asn Tyr
                515                 520                 525

Ala Glu Ala Lys Asp Val Phe Leu Gly Met Phe Leu Tyr Glu Tyr Ala
        530                 535                 540

Arg Arg His Pro Asp Tyr Ser Val Val Leu Leu Leu Arg Leu Ala Lys
545                 550                 555                 560

Thr Tyr Glu Thr Thr Leu Glu Lys Cys Cys Ala Ala Ala Asp Pro His
                565                 570                 575

Glu Cys Tyr Ala Lys Val Phe Asp Glu Phe Lys Pro Leu Val Glu Glu
            580                 585                 590

Pro Gln Asn Leu Ile Lys Gln Asn Cys Glu Leu Phe Glu Gln Leu Gly
                595                 600                 605

Glu Tyr Lys Phe Gln Asn Ala Leu Leu Val Arg Tyr Thr Lys Lys Val
        610                 615                 620

Pro Gln Val Ser Thr Pro Thr Leu Val Glu Val Ser Arg Asn Leu Gly
625                 630                 635                 640

Lys Val Gly Ser Lys Cys Cys Lys His Pro Glu Ala Lys Arg Met Pro
                645                 650                 655

Cys Ala Glu Asp Tyr Leu Ser Val Val Leu Asn Gln Leu Cys Val Leu
            660                 665                 670

His Glu Lys Thr Pro Val Ser Asp Arg Val Thr Lys Cys Cys Thr Glu
                675                 680                 685

Ser Leu Val Asn Arg Arg Pro Cys Phe Ser Ala Leu Glu Val Asp Glu
        690                 695                 700

Thr Tyr Val Pro Lys Glu Phe Asn Ala Glu Thr Phe Thr Phe His Ala
705                 710                 715                 720
```

Asp Ile Cys Thr Leu Ser Glu Lys Glu Arg Gln Ile Lys Lys Gln Thr
              725                 730                 735

Ala Leu Val Glu Leu Val Lys His Lys Pro Lys Ala Thr Lys Glu Gln
              740                 745                 750

Leu Lys Ala Val Met Asp Asp Phe Ala Ala Phe Val Glu Lys Cys Cys
              755                 760                 765

Lys Ala Asp Asp Lys Glu Thr Cys Phe Ala Glu Glu Gly Lys Lys Leu
              770                 775                 780

Val Ala Ala Ser Gln Ala Ala Leu Gly Leu
785                 790

<210> SEQ ID NO 4
<211> LENGTH: 2382
<212> TYPE: DNA
<213> ORGANISM: Unknown
<220> FEATURE:
<223> OTHER INFORMATION: Sequence encoding fusion protein
      Slit2D2(C386S)-HSA

<400> SEQUENCE: 4

| | | | | |
|---|---|---|---|---|
| ttgcactgcc | ctgccgcctg | tacctgtagc | aacaatatcg | tagactgtcg | tgggaaaggt | 60 |
| ctcactgaga | tccccacaaa | tcttccagag | accatcacag | aaatacgttt | ggaacagaac | 120 |
| acaatcaaag | tcatccctcc | tggagctttc | tcaccatata | aaaagcttag | acgaattgac | 180 |
| ctgagcaata | atcagatctc | tgaacttgca | ccagatgctt | tccaaggact | acgtctctg  | 240 |
| aattcacttg | tcctctatgg | aaataaaatc | acagaactcc | ccaaaagttt | atttgaagga | 300 |
| ctgttttcct | tacagctcct | attattgaat | gccaacaaga | taaacagtct | tcgggtagat | 360 |
| gcttttcagg | atctccacaa | cttgaacctt | ctctccctat | atgacaacaa | gcttcagacc | 420 |
| atcgccaagg | ggaccttttc | acctcttcgg | gccattcaaa | ctatgcattt | ggcccagaac | 480 |
| ccctttattt | gtgactgcca | tctcaagtgg | ctagcggatt | atctccatac | caacccgatt | 540 |
| gagaccagtg | gtgcccgttg | caccagcccc | cgccgcctgg | caaacaaaag | aattggacag | 600 |
| atcaaaagca | agaaattccg | ttgttcagat | gcacacaaga | gtgaggttgc | tcatcggttt | 660 |
| aaagatttgg | gagaagaaaa | tttcaaagcc | ttggtgttga | ttgcctttgc | tcagtatctt | 720 |
| cagcagtgtc | catttgaaga | tcatgtaaaa | ttagtgaatg | aagtaactga | atttgcaaaa | 780 |
| acatgtgttg | ctgatgagtc | agctgaaaat | tgtgacaaat | cacttcatac | ccttttggga | 840 |
| gacaaattat | gcacagttgc | aactcttcgt | gaaacctatg | gtgaaatggc | tgactgctgt | 900 |
| gcaaaacaag | aacctgagag | aaatgaatgc | ttcttgcaac | acaaagatga | caacccaaac | 960 |
| ctccccccgat | tggtgagacc | agaggttgat | gtgatgtgca | ctgcttttca | tgacaatgaa | 1020 |
| gagacatttt | tgaaaaaata | cttatatgaa | attgccagaa | gacatcctta | cttttatgcc | 1080 |
| ccggaactcc | ttttctttgc | taaaaggtat | aaagctgctt | ttacagaatg | ttgccaagct | 1140 |
| gctgataaag | ctgcctgcct | gttgccaaag | ctcgatgaac | ttcgggatga | agggaaggct | 1200 |
| tcgtctgcca | aacagagact | caagtgtgcc | agtctccaaa | aatttggaga | aagagctttc | 1260 |
| aaagcatggg | cagtagctcg | cctgagccag | agatttccca | aagctgagtt | tgcagaagtt | 1320 |
| tccaagttag | tgacagatct | taccaaagtc | cacacggaat | gctgccatgg | agatctgctt | 1380 |
| gaatgtgctg | atgacagggc | ggaccttgcc | aagtatatct | gtgaaaatca | agattcgatc | 1440 |
| tccagtaaac | tgaaggaatg | ctgtgaaaaa | cctctgttgg | aaaaatccca | ctgcattgcc | 1500 |
| gaagtggaaa | atgatgagat | gcctgctgac | ttgccttcat | tagctgctga | ttttgttgaa | 1560 |

```
agtaaggatg tttgcaaaaa ctatgctgag gcaaaggatg tcttcctggg catgtttttg    1620
tatgaatatg caagaaggca tcctgattac tctgtcgtgc tgctgctgag acttgccaag    1680
acatatgaaa ccactctaga gaagtgctgt gccgctgcag atcctcatga atgctatgcc    1740
aaagtgttcg atgaatttaa acctcttgtg gaagagcctc agaatttaat caaacaaaat    1800
tgtgagcttt ttgagcagct tggagagtac aaattccaga atgcgctatt agttcgttac    1860
accaagaaag taccccaagt gtcaactcca actcttgtag aggtctcaag aaacctagga    1920
aaagtgggca gcaaatgttg taaacatcct gaagcaaaaa gaatgccctg tgcagaagac    1980
tatctatccg tggtcctgaa ccagttatgt gtgttgcatg agaaaacgcc agtaagtgac    2040
agagtcacca aatgctgcac agaatccttg gtgaacaggc gaccatgctt ttcagctctg    2100
gaagtcgatg aaacatacgt tcccaaagag tttaatgctg aaacattcac cttccatgca    2160
gatatatgca cactttctga gaaggagaga caaatcaaga aacaaactgc acttgttgag    2220
ctcgtgaaac acaagcccaa ggcaacaaaa gagcaactga aagctgttat ggatgatttc    2280
gcagcttttg tagagaagtg ctgcaaggct gacgataagg agacctgctt tgccgaggag    2340
ggtaaaaaac ttgttgctgc aagtcaagct gccttaggct ta                      2382
```

FUSION PROTEIN SLIT2D2(C386S)-HSA AND USE THEREOF IN TREATMENT OF FIBROTIC DISEASES

CROSS-REFERENCE TO RELATED APPLICATION

This application is a continuation application of International patent application No. PCT/CN2017/114599, filed on Dec. 5, 2017, which claims the benefit and priority of Chinese patent application No. CN201611110752.9, filed on Dec. 6, 2016, each of which is incorporated herein by reference in its entirety and for all purposes.

FIELD OF THE INVENTION

The present invention relates to the field of biomedical technology, in particular to a fusion protein Slit2D2 (C386S)-HSA and use thereof in the treatment and/or prevention of fibrotic diseases.

BACKGROUND OF THE INVENTION

Fibrosis may occur in a variety of organs, and its main pathological changes are the increase of fibrous connective tissue in organ tissues, and the decrease of parenchymal cells. The continuous progress of fibrosis may lead to organ structural destruction and functional decline, or even failure, which seriously threatens human health and life. Any cause, as long as it can cause tissue cell damage, may lead to degeneration, necrosis and inflammatory response of tissue cells. If the damage is slight, the normal parenchyma cells around the damaged cells will undergo proliferative repair, which can completely restore the normal structure and function. However, if the damage is so severe or repeated that it exceeds the regeneration ability of the parenchymal cells around the damaged cells, the interstitial fibrous connective tissue (extracellular matrix) will repair the damaged tissue with a large amount of hyperplasia, leading to the pathological changes of fibrosis. Therefore, fibrosis is essentially a repairing response to tissue injury to maintain the relative integrity of tissues and organs. Although the proliferating fibrous connective tissue may repair the defect, it does not have the structure and function of the original organ parenchymal cells. If this repairing response is excessive, too strong, and out of control, it will cause fibrosis of the organs and lead to a decline in the function of the organs. Thus, it can be seen that fibrosis refers to a pathological process which involves necrosis of organ parenchymal cells, abnormal increase and excessive deposition of extracellular matrix in tissues due to inflammation. The slight pathological process causes fibrosis, and on the other hand the severe pathological process causes structural destruction and organ sclerosis. Worldwide, tissue fibrosis is the leading cause of disability and death in many diseases. According to the relevant statistics of the United States, nearly 45% of the patients who died from various diseases in this country can be attributed to tissue fibroproliferative diseases. Fibrotic diseases include pulmonary fibrosis, liver fibrosis, and renal fibrosis, etc.

At present, there are few therapeutic drugs for fibrotic diseases. Taking pulmonary fibrosis as an example, currently the drugs approved by the FDA are only Esbriet (pirfenidone), developed and produced by InterMune, Inc., and OFEV® (Nindedanib), developed and produced by Boehringer-Ingelheim, German. However, currently these two drugs are not ideal for patients.

Neuronal migration protein, Slit, is an evolutionarily highly conserved secreted extracellular matrix glycoprotein with a molecular weight of about 200 kD, which plays a guiding role for axon growth and neuronal migration. The gene of Slit cloned in mammals has three members, Slit1, Slit2 and Slit3, which is composed of an extracellular signal peptide at N-terminal, four leucine-rich repeats (LRRs), also named as D1-D4 domains, a plurality of EGF (epidermal growth factor)-like repeats (seven in Drosophilidae and nine in vertebrate), a laminin G-like domain and a cysteine-rich C-terminal region, and among which Slit-2 is the most important. Robo protein family, a receptor family of Slit, is a single-channel transmembrane receptor. Slit functions by binding with the receptor Robo, and the LRRs are the regions for the binding of Slit protein with the receptor Robo. At present, there are literatures reporting that Slit2 protein may inhibit migration of neutrophils.

Research shows that Slit protein plays a major role in angiogenesis, tumor cell migration, leukocyte chemotaxis, etc. In U.S. Pat. No. 8,399,404 B2, Slit protein and nucleic acid are used for the treatment of platelet coagulation and other related disorders, and a vascular device using Slit protein coating and cells capable of expressing a Slit protein are also disclosed. Patent No. WO2009105457 discloses a method and a composition for the diagnosis, research and treatment of cancer, involving the effective use of Slit2 protein, as a tumor marker, as a diagnostic marker and a clinical target for prostate cancer.

Tole et al., through the study, have found that the Slit2 protein inhibits the migration of neutrophils by inhibiting actin filament formation and cell polarization induced by chemokines (The axonal repellent, Slit2, inhibits directional migration of circulating neutrophils. J Leukoc Biol. 2009, 86(6): 1403-15).

Hohenester has found that Slit-Robo interaction is formed by IG1 domain of Robo binding with D2 domain of Slit (Structural insight into Slit-Robo signaling. Biochemical Society Transactions. 2008, 36: 251-256), therefore, D2 domain is very important for the biology activity of Slit protein.

Chinese Patent application CN201310150884.4 reports a fusion protein formed by D1-2 sequences of Slit2 protein prepared by using gene recombinant technology. The fusion protein facilitates the correct folding of the LRR and the formation of an active functional polypeptide for the research and application of the Slit2 protein.

WO2014/194402A1 reports that the Slit2 molecule can be used for the treatment of fibrotic diseases. Pilling D et al. explored the mechanism by which Slit2 molecules inhibit fibrosis (Fibroblasts secrete Slit2 to inhibit fibrocyte differentiation and fibrosis. PNAS. 2014, 111(51): 18291-6).

Protein drugs with a molecular weight less than 20 kD could be easily filtrated by glomerular in the metabolic process, leading to a short half-life in vivo. In order to achieve a therapeutic effect, frequent or large doses of administration are often required, which causes a great inconvenience to the patient. Human serum albumin (HSA) is a stable "inert" protein that is difficult to permeate through the glomeruli under normal physiological conditions and has a half-life in serum of 14-21 days, which can be used as a carrier to bind to other factors in the blood, including biologically active proteins, thereby maintaining or extending the biological activity of the other factors in vivo. It is an effective way to improve the half-life of small molecular peptides or protein drugs by the fusion of small molecular peptides or protein drugs with HSA. Compared with other methods, construction of a long-acting albumin fusion protein drug could avoid the complicated chemical modification and processing, and thus has the advantages of easy operation and better economy.

In order to overcome the deficiencies in the prior art, the present invention provides a fusion protein for treating and/or preventing a fibrotic disease and use thereof.

SUMMARY OF THE INVENTION

An aspect of the present invention provides a polypeptide or protein comprising or consisting of a D2 domain of a Slit2 protein (hereinafter referred to as Slit2D2), wherein the cysteine in the Slit2D2, corresponding to the 5th cysteine of the Slit2 protein, is mutated to other amino acid or deleted.

Preferably, the Slit2 protein is a Slit2 protein derived from a mammal, preferably human, and the cysteine in the Slit2D2, corresponding to the 5th cysteine of the Slit2 protein, is located at the position 386 of the Slit2 protein.

Preferably, the other amino acid is a polar amino acid, preferably selected from the group consisting of amino acid residues of Ser, Gln, Thr, Asn and Tyr.

More preferably, the polypeptide or protein comprises or consists of the amino acid sequence as shown in SEQ ID NO: 1.

Preferably, the polypeptide or protein further comprises an amino acid sequence derived therefrom by substituting and/or deleting and/or adding one or several amino acid residues and having the same function; and more preferably, there may be less than 10 amino acid residues changed for the substitution and/or deletion and/or addition.

Another aspect of the present invention provides a nucleotide encoding the above polypeptide or protein.

Preferably, the nucleotide has a nucleotide sequence as shown in SEQ ID NO: 2 or degenerate sequences thereof.

Yet another aspect of the present invention provides a fusion protein comprising the above polypeptide or protein.

Preferably, the fusion protein further comprises human serum albumin (HSA).

In a preferred embodiment of the present invention, the fusion protein is Slit2D2(C386S)-HSA, which is obtained by linking the above polypeptide or protein with HSA directly or through a linker peptide.

The direct linkage means that the polypeptide or protein is directly linked to the N-terminus of the HSA protein via its C-terminus, or the polypeptide or protein is directly linked to the C-terminus of the HSA protein through its N-terminus, without any linker peptide therebetween.

Preferably, the fusion protein comprises or consists of the amino acid sequence as shown in SEQ ID NO: 3.

Another aspect of the present invention provides a nucleotide encoding the fusion protein described above.

Preferably, the nucleotide comprises or consists of the nucleotide sequence as shown in SEQ ID NO: 4.

Another aspect of the present invention provides a vector comprising the above nucleotide encoding the polypeptide or protein, or the nucleotide encoding the fusion protein.

Yet another aspect of the present invention provides a host cell comprising the above nucleotide encoding the polypeptide or protein, the nucleotide encoding the fusion protein, or the vector.

Preferably, the host cell is one comprising the above vector.

Another aspect of the present invention provides a preparation method of the above fusion protein, including the steps of culturing the above host cell and, optionally, isolating and purifying.

Preferably, the above preparation method includes the following steps:
(1) constructing and verifying a recombinant vector;
(2) preparing and fermenting a transformant;
(3) isolating and purifying the fusion protein;
optionally, (4) identifying the fusion protein.

Preferably, the construction of the recombinant vector described in the step (1) includes inserting a gene fragment of the fusion protein into an expression vector using a T/A clone to obtain a recombinant vector.

Preferably, the gene of the fusion protein is obtained by total gene synthesis.

Preferably, the expression vector is a pCDNA plasmid. In a preferred embodiment of the present invention, the expression vector is pCDNA3.4.

Preferably, the verification of the recombinant vector described in the step (1) includes transforming the recombinant vector into a host cell 1, screening positive clones, confirming that the vector is successfully constructed, and preserving.

Preferably, the host cell 1 is *Escherichia coli*. In a preferred embodiment of the present invention, the host cell 1 is *Escherichia coli* TOP10.

Preferably, the step (2) includes extracting the recombinant vector verified by step (1), transfecting it into a host cell 2, and fermenting.

In a preferred embodiment of the present invention, the host cell 2 is an ExpiCHO-S™ cell.

Preferably, the isolation and purification of the fusion protein described in step (3) includes performing by affinity chromatography and/or ion exchange chromatography.

Another aspect of the present invention provides a pharmaceutical composition comprising the above polypeptide or protein and/or the fusion protein, optionally, and a pharmaceutically acceptable excipient.

The pharmaceutical composition of the present invention may be a tablet (including a sugar-coated tablet, a film-coated tablet, a sublingual tablet, an orally disintegrating tablet, an oral tablet, etc.), a pill, powder, a granule, a capsule (including a soft capsule, a microcapsule), a lozenge, a syrup, a liquid, an emulsion, a suspension, a controlled release formulation (for example, a transient release formulation, a sustained release formulation, a sustained release microcapsule), an aerosol, a film (for example, an orally disintegrating film, an oral mucosa-adhesive film), an injection (for example, a subcutaneous injection, an intravenous injection, an intramuscular injection, an intraperitoneal injection), an intravenous drip, a transdermal absorption formulation, an ointment, a lotion, an adhesive formulation, a suppository (for example, a rectal suppository, a vaginal suppository), a small pill, a nasal formulation, a pulmonary formulation (an inhalation), an eye drop, etc., an oral or parenteral formulation (for example, through intravenous, intramuscular, subcutaneous, intra-organ, intranasal, intradermal, instillation, intracerebral, intrarectal and other dosage forms, the drug is given to the vicinity of a tumor and directly given to the lesion). Preferably, the pharmaceutical composition is an injection.

The pharmaceutically acceptable excipient of the present invention is preferably a pharmaceutically acceptable excipient for injection, such as isotonic sterile saline solution (sodium dihydrogen phosphate, disodium hydrogen phosphate, sodium chloride, potassium chloride, calcium chloride, magnesium chloride, etc., or a mixture of the above salts). Or, for a dried, for example, freeze-dried composition, sterile water or physiological saline may be suitably added thereto to form an injectable solute.

Another aspect of the present invention provides a use of the above polypeptide or protein, the fusion protein, the pharmaceutical composition for the preparation of a medicament for preventing and/or treating a fibrotic disease or sepsis.

Preferably, the fibrotic disease is pulmonary fibrosis.

Preferably, the sepsis is severe sepsis or septic shock.

In the present invention, the term "prevention", "preventing" or "treatment", "treating" includes therapeutic or prophylactic treatment or measures with the goal of preventing or slowing down a targeted pathological condition or disorder. A subject is successfully "prevented" or "treated" if, after receiving a therapeutic amount of the fusion protein of the present invention according to the method of the present invention, the subject shows an observable and/or measurable reduction or disappearance of one or more signs and symptoms of a particular disease.

In the fusion protein provided by the present invention, only the Slit2D2 domain is retained, which has a smaller molecular weight and better tissue permeability, and is more easily used for drug development than the Slit2 molecule. On the basis of analysis and experiment, the amino acid residue in the Slit2D2 domain is mutated, which improves the stability of the fusion protein compared with the native protein. The above fusion protein is obtained by fusing Slit2D2 (C386S) with HSA protein, which prolongs the metabolism time of the drug while improving the stability of the drug. The fusion protein provided by the present invention is more effective than the positive control drug in the prevention and treatment of fibrotic diseases, particularly pulmonary fibrosis, and shows good drug-forming properties.

DETAILED DESCRIPTION OF THE INVENTION

The technical solutions in the embodiments of the present invention will be clearly and completely described in the following with reference to the accompanying drawings in the embodiments of the present invention. It is apparent that the described embodiments are only a part of the embodiments of the present invention, and not all of the embodiments. All other embodiments obtained by those skilled in the art based on the embodiments of the present invention without creative efforts are within the scope of the present invention.

Example 1

Preparation of the Fusion Protein Slit2D2(C386S)-HSA

Based on the known sequence of Slit2 [GenBank: EAW92793.1], the second domain of Slit2, Slit2D2, was analyzed, designed and constructed, and Slit2D2(C386S) was designed as shown in SEQ ID NO: 1, and further, the sequences encoding Slit2D2(C386S) and Slit2D2(C386S)-HSA were designed as shown in SEQ ID NO: 2 and SEQ ID NO: 4, respectively.

Figure 1:
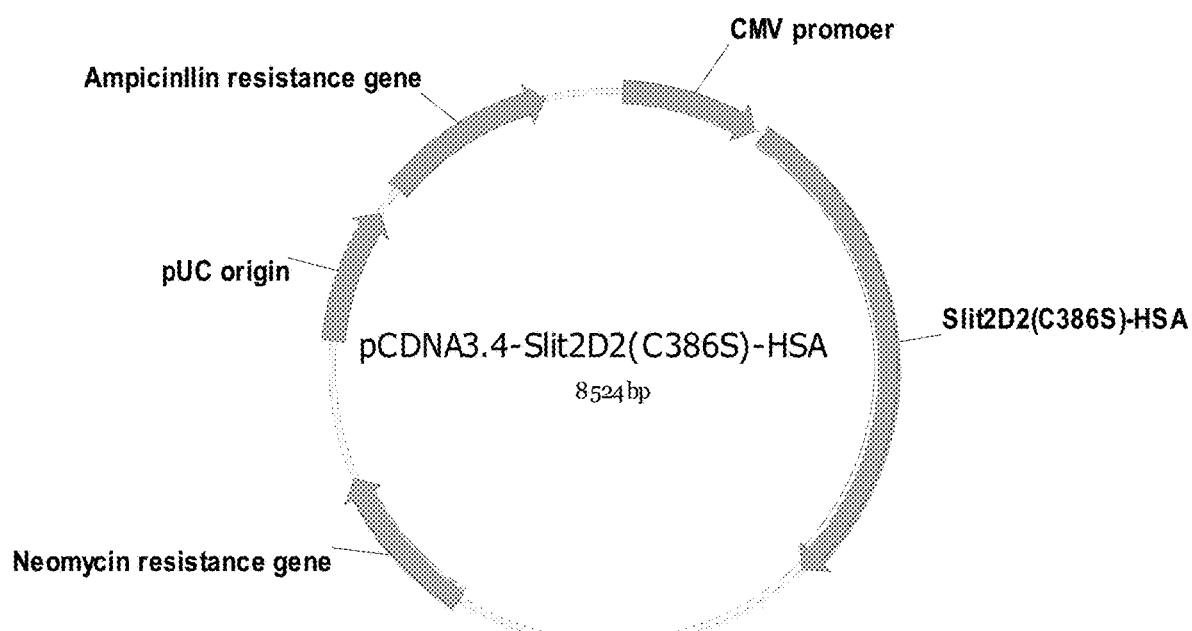
FIG. 1 illustrates a map of the recombinant vector pCDNA3.4-Slit2D2(C386S)-HSA provided in Example 1 of the present invention.

The encoding sequence of Slit2D2(C386S)-HSA was obtained by total gene synthesis, and inserted into pCDNA3.4 (Brand: Thermo, Art. No.: A14697) expression vector by T/A clone. The map of the recombinant vector pCDNA3.4-Slit2D2(C386S)-HSA is shown in FIG. 1. The above recombinant expression vector was transformed into Escherichia coli TOP10, and then inoculated into a solid medium containing ampicillin (AMP) for propagation. Positive clones were screened, and the vector was confirmed to be successfully constructed by sequencing, and preserved.

The recombinant plasmid in E. coli TOP10 was extracted with an endotoxin-free plasmid extraction kit for transfection into ExpiCHO-S™ cells (Gibco Catalog No. A29127). ExpiCHO-S™ cells were cultured and transfected with the recombinant plasmid when the cell density reached $4\times10^6$-$6\times10^6$ cells/ml (transfection reagent: ExpiFectamine™ CHO Transfection Kit, Gibco Catalog No. A29129). After transfection, the cells were cultured for 10 days. The supernatant was collected, centrifuged at high speed, and purified through a HSA affinity chromatography (Filler of chromatography: Thermo, Art. No.: 191297050) and a weak anion exchange chromatography (Brand: Smart-Lifesciences, Art. No.: DEAE Beads 6FF, SI005025) to give the Slit2D2(C386S)-HSA fusion protein.

Figure 2:
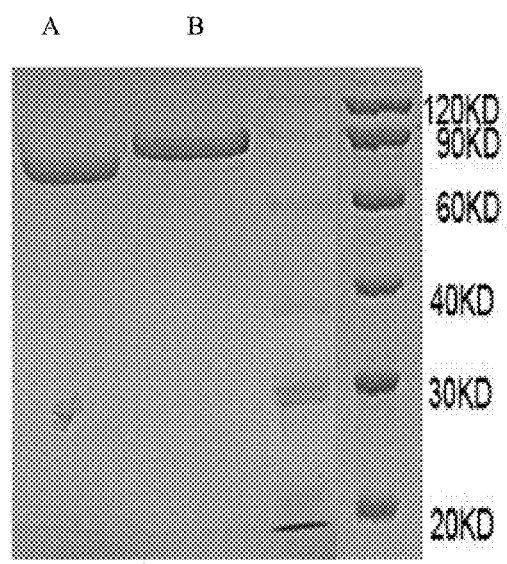
FIG. 2 illustrates a photograph showing the SDS-PAGE protein electrophoresis detection for the Slit2D2(C386S)-HSA fusion protein provided in Example 1 of the present invention; wherein, A: Slit2D2(C386S)-HSA denatured protein; and B: Slit2D2(C386S)-HSA non-denatured protein.
Figure 3:
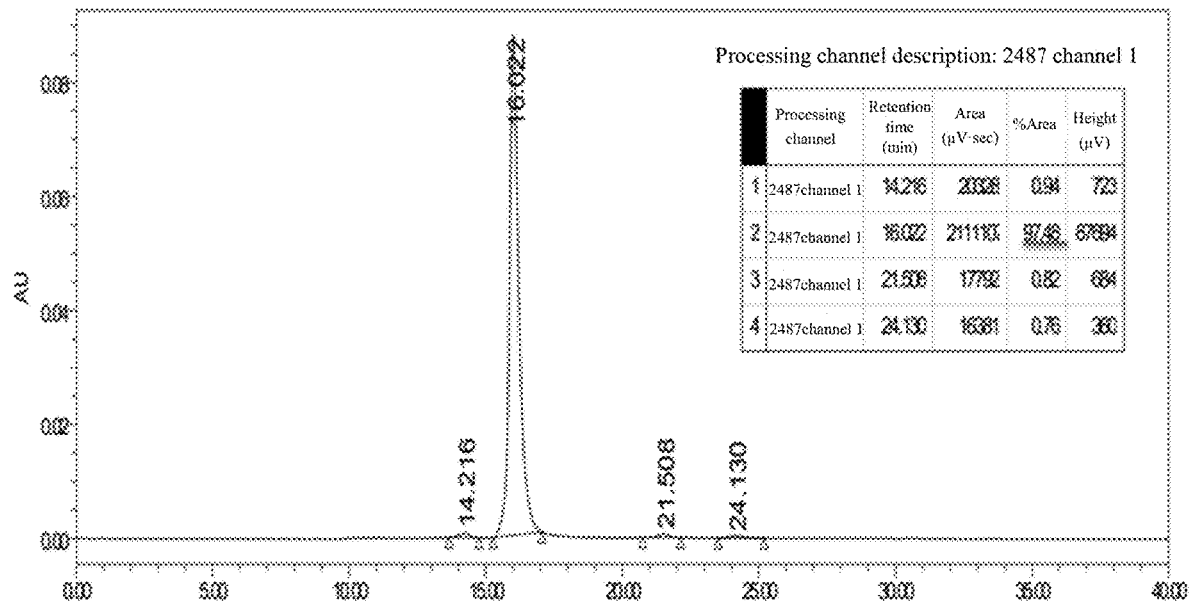
FIG. 3 illustrates the SEC-HPLC detection spectrum of the Slit2D2(C386S)-HSA fusion protein provided in Example 1 of the present invention.

The molecular weight of the purified fusion protein was determined by SDS-PAGE method. The purity of the fusion protein was determined by SEC-HPLC. The results of SDS-PAGE and the sepctra of SEC-HPLC are shown in FIGS. 2 and 3, respectively. It can be seen from FIG. 2 that the recombinant expression vector expressing the fusion protein Slit2D2(C386S)-HSA has been successfully constructed, and the fusion protein Slit2D2(C386S)-HSA was expressed and purified in the host cell, purity: 97.48%.

Example 2

Determination of the Affinity of the Fusion Protein to Target Robo1 Protein by SPR The affinity constant between the protein and Robo1 protein was detected by SPR (Surface Plasmon resonance BIAcore 200) method. The Robo1 protein (ORIGEN, Art. No.: TP327713) was bound to a CM5 chip, and the interaction between the fusion protein Slit2D2(C386S)-HSA (prepared in Example 1), Slit2D2-HSA (as disclosed in Patent Application PCT/CN2015/092079), and the receptor protein Robo1 were analyzed. Kinetic measurements were performed according to the method referred by Canziani et al. (2004, Anal. Biochem. 325: 301-307). Furthermore, the affinity of the Slit2N protein (Slit2N is a protein having a molecular weight of about 120 kDa at the N-terminus of the Slit2 protein) to Robo1 protein was also determined by the same method. The results are shown in Table 1.

TABLE 1

Results of the affinity of the fusion protein to receptor Robo1 determined by SPR

| No. | Protein | Ka(1/Ms) | KD(M) | Kd(nM) |
|---|---|---|---|---|
| 1 | Slit2N | $7.436 \times 10^5$ | $3.394 \times 10^{-1}$ | 4.5 |
| 2 | Slit2D2-HSA | $1.771 \times 10^5$ | $5.099 \times 10^{-4}$ | 2.8 |
| 3 | Slit2D2(C386S)-HSA | $8.647 \times 10^5$ | $1.167 \times 10^{-1}$ | 1.35 |

The results show that both of the designed and constructed fusion proteins Slit2D2-HSA and Slit2D2(C386S)-HAS have good affinity to the receptor Robo1 protein, which have similar properties to the Slit2N protein.

Example 3

Determination of the Protein Stability by ELISA

1. Reagents

Neutroavidin-HRP diluent;

Coating buffer: –0.16% $Na_2CO_3$; –0.3% $NaHCO_3$; –pH 9.8;

Washing buffer: PBS containing–0.1% Tween20;

Blocking buffer: Washing buffer containing–1% Goat Serum;

TMB: purchased from Shanghai Beyotime Biotechnology Co., Ltd.;

Stop solution: purchased from Shanghai Beyotime Biotechnology Co., Ltd.;

Note: All antibodies were diluted with the blocking buffer.

2. Experimental Process

Figure 4:
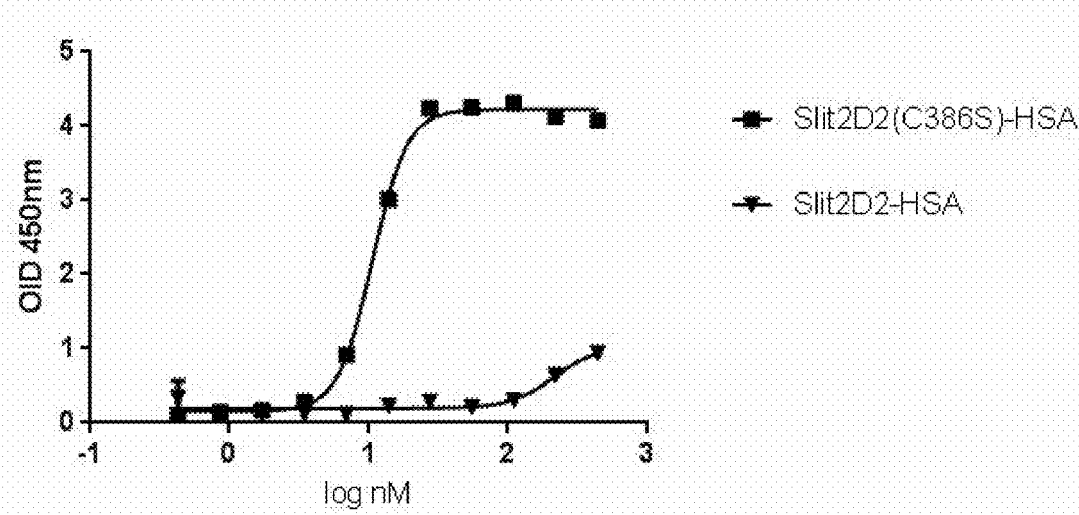
FIG. 4 illustrates a graph showing the results of stability test of the fusion protein according to Example 3 of the present invention.

The Robo1 protein was diluted to 1 µg/ml, and was used to coat a plate at 100 µl/well overnight at 4° C. The plate was washed 3 times with Washing buffer, and blocked with Blocking buffer (200 µl/well) for 2 hours at room temperature, then washed 3 times with Washing buffer. The test samples (fusion protein Slit2D2(C386S)-HSA (prepared in Example 1), Slit2D2-HSA (as disclosed in Patent application PCT/CN2015/092079) 100 µl) were separately added and incubated at room temperature for 2 hours. The plate was washed 3 times with Washing buffer. Anti-HSA-HRP antibody was diluted to 1 µg/ml at 1:10000, and was used to coat the plate at 100 µl/well, and then incubated for 1 hour at room temperature. The plate was washed 3 times with Washing buffer. 100 µl of TMB was added to each well to develop color for 15 minutes. Color development was stopped by adding 50 µl of Stop solution to each well. The absorbance at 450 nm was read, and the experimental results are shown in FIG. 4.

The results show that the $EC_{50}$ values of Slit2D2(C386S)-HSA and Slit2D2-HSA were 10.56 and 214.6 nM, respectively, indicating that Slit2D2(C386S)-HSA has better stability than Slit2D2-HSA protein after treatment.

Example 4

Pharmacokinetic Assay

1. Experimental Animals

1.1 Basic Information

Lines and sources: cynomolgus monkeys, Guangxi Xiongsen Primate Laboratory Animal Breeding Development Co., Ltd.

Animal Stock Centre: 999M-014, non-naïve;
Age of experimental animals: 3.0-4.5 years old;
Body weight of animals before the start of the test: 2.75-3.00 kg;
Number and gender: 2 males, and 2 females.

1.2 Animal Feeding

Each animal was housed in a single cage (stainless steel mobile cage) in an environmentally controlled room in the test facility. The temperature and relative humidity of the room were recorded twice a day. The temperature and relative humidity during the test were in the range of 18 to 26° C. and 40 to 70%, respectively. The actual temperature and relative humidity records were saved in the original record. The animals are illuminated, alternating between light and dark, for about 12 hours each day.

The compound feed (Production batch numbers: 1650230222 and 1650230527, expiry dates: 2016 May 21 and 2016 Aug. 26, respectively, purchased from Beijing Huafukang Bioscience Co., Inc.) was freely fed by the experimental monkeys during the test. The compound feed for the experimental monkeys was tested by a third party (PONY) commissioned by the test facility to determine specific microorganisms, heavy metals and pesticide residues in the feed. The reverse osmosis water was supplied to each animal through a water bottle without interruption. The pH, hardness, heavy metals and microorganisms of the drinking water were regularly tested by the applicant and the commissioned third party. The test results of feed and water were in compliance with the relevant national regulations.

2. Main Computer Software or Computer System Used in the Test

TABLE 2

| Main computer software or computer system used in the test |  |
| --- | --- |
| Medicilon Pharmaceutical Technology (Shanghai) Co., Ltd. | |
| Microsoft ®Office 2003 Professional Edition | A set of utilities for working |
| Microsoft ®Office 2007 Professional Edition: | with text and data. Including |
| 3. Test method | Word ® and Excel ®, etc. |
| 3.1 Test design | Phoenix Pharmacokinetic Software |

TABLE 3

Test design table

| Animal No. | Group | Gender | Test substance | Body weigth (kg) | Dosage of administration (mg/kg) | Concentration of administration (mg/mL) | Volume of administration (mL/kg) | Amount of administration (mL) | Route of administration* |
| --- | --- | --- | --- | --- | --- | --- | --- | --- | --- |
| 101 | 1 | Male | Slit2D2(C386S)-HSA | 2.70 | 2.0 | 1.0 | 2.0 | 5.4 | IV |
| 102 | 1 | Male | Slit2D2(C386S)-HSA | 2.65 | 2.0 | 1.0 | 2.0 | 5.4 | IV |
| 103 | 1 | Female | Slit2D2(C386S)-HSA | 2.75 | 2.0 | 1.0 | 2.0 | 5.6 | IV |
| 104 | 1 | Female | Slit2D2(C386S)-HSA | 2.60 | 2.0 | 1.0 | 2.0 | 5.2 | IV |

*Single administration.

3.2 Administration

3.2.1 Mode of Administration

The test substance was administered in a single dose by intravenous injection.

3.3 Detection Indicators

3.3.1 Observation

During the test, all animals were observed at various time points in the blood collection and before administration, including morbidity, damage, death rate and food and water supply.

3.4 Pharmacokinetics and Immunogenicity Studies

3.4.1 Number of Animals

All animals did not need to be fasted before sampling.

3.4.2 Biological Sample Collection

Blood was collected through the eyelids, and about 2.0 mL of each sample was collected and placed in an Eppendorf tube containing 200 μL of 3.8% sodium citrate, and then placed on ice.

3.4.2.1 Sampling Time

Sampling was performed once before administration (0 h), and at 3 h, 6 h, 12 h, 24 h and 4th, 6th, 8th, 11th, 14th, 17th, 19th, 22nd, 26th, 36th, and 43th day after administration, with a total of 17 time points.

3.4.3 Plasma Sample Processing

The blood samples were collected and centrifuged to separate plasma (centrifugation conditions: 8000 rpm, 6 minutes, 2-8° C.). The contents of the label included: the subject number of Medicilon Pharmaceutical Technology (Shanghai) Co., Ltd., relevant test days, serial number of animals, date, and sampling time point. The collected plasma samples were stored in a refrigerator at ≤−65° C. before analysis. After analysis, the remaining plasma samples were stored in the refrigerator at ≤−65° C. for subsequent processing.

3.4.4 Sample Analysis

The biological sample analysis method and analysis of all samples were performed by the analytical laboratory of Medicilon Pharmaceutical Technology (Shanghai) Co., Ltd. Each plate in the sample analysis must contain a standard curve. At least ¾ of the points and not less than 6 non-zero concentration points (without anchor points) constituting the standard curve should meet the acceptance criteria for method validation. Each plate should also contain at least 2 sets and each set comprised at least 3 quality control samples of different concentration levels (high-concentration quality control, intermediate-concentration quality control, and low-concentration quality control). It was further required that the quality control sample, which accounts for 67% (⅔) of the total and has each concentration level not lower than 50%, should have a precision within 20% and an accuracy of 80-120%.

3.5 Disposal of the Animals

Blank plasma was collected from all the experimental animals at the end of the test and transferred to the animal stock centre of the test facility. The disposal of the animal was recorded.

4. Test Results

4.1 Observation

No abnormal findings were observed during the test.

4.2 Determination of Plasma Drug Concentration

Figure 5:
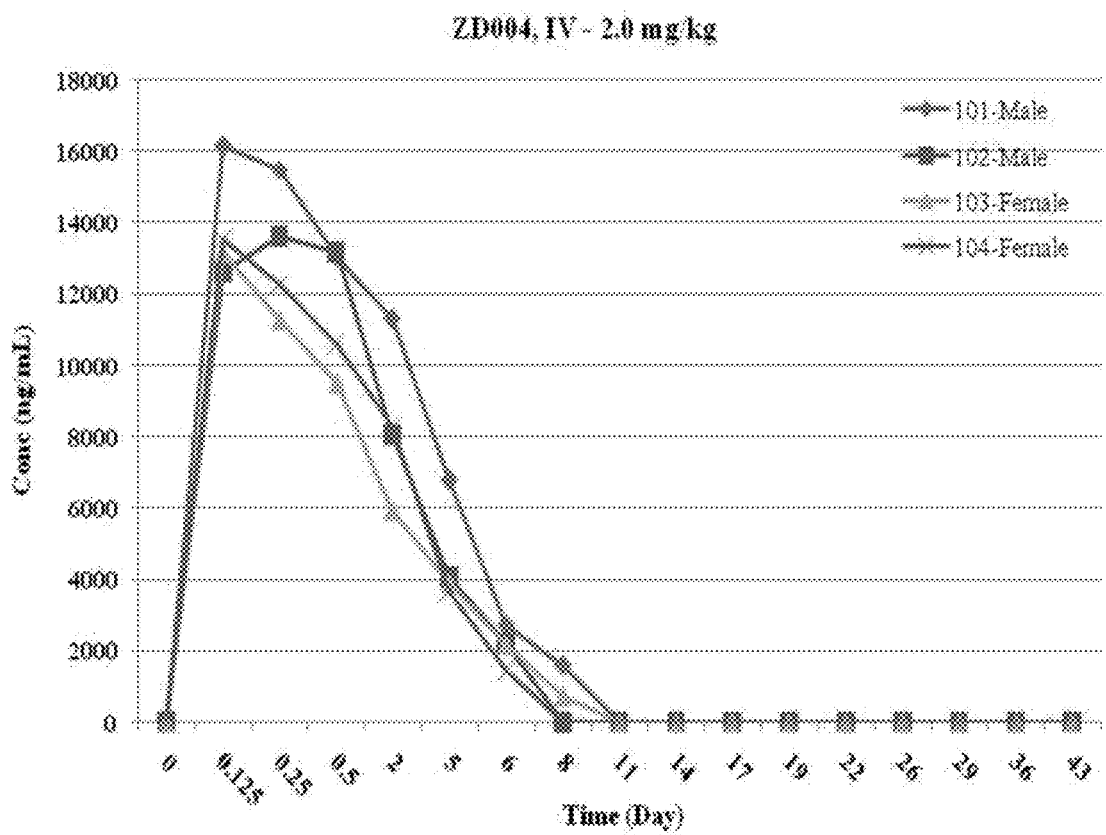
FIG. 5 illustrates a graph showing the individual plasma drug concentration-time curve of cynomolgus monkeys given a single intravenous administration of 2 mg/kg of SLIT2D2(C386S)-HSA according to Example 4 of the present invention.
Figure 6:
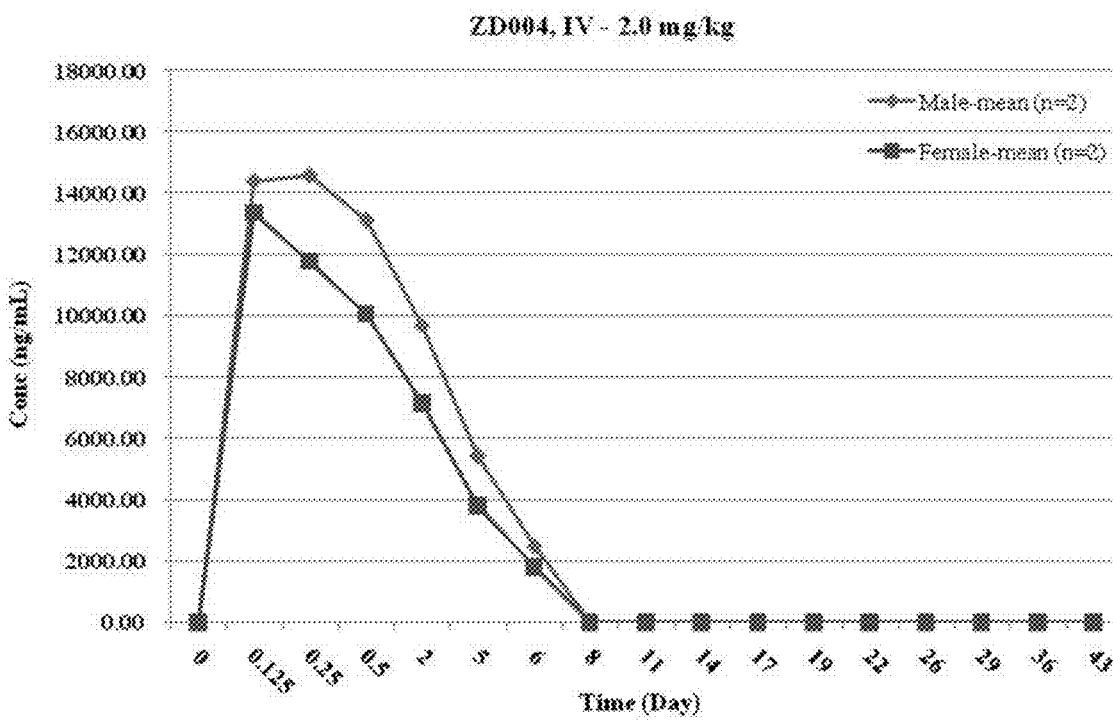
FIG. 6 illustrates a graph showing the mean plasma drug concentration-time curve for males and females of cynomolgus monkeys given a single intravenous administration of 2 mg/kg of SLIT2D2(C386S)-HSA according to Example 4 of the present invention.

The determination results of plasma drug concentration of cynomolgus monkeys after intravenous injection of Slit2D2 (C386S)-HSA are shown in Table 4. The drug concentration-time curves are shown in FIGS. 5 and 6.

Plasma drug concentration-time trends in animals of different genders (except #101-Male) in the Slit2D2 (C386S)-HSA group are basically consistent or vary to some extent.

TABLE 4

Plasma drug concentration of cynomolgus monkeys after a single intravenous administration of 2 mg/kg of Slit2D2(C386S)-HSA

| | Slit2D2(C386S)-HSA-IV-2 mg/kg Plasma drug concentration (ng/mL) | | | | | |
|---|---|---|---|---|---|---|
| Time point (day) | 101-Male | 102-Male | 103-Female | 104-Female | Mean | SD |
| 0 | 0.00 | 0.00 | 0.00 | 0.00 | NA | NA |
| 0.125 | 16151.832 | 12629.116 | 13162.76 | 13541.873 | 13871.40 | 1565.72 |
| 0.25 | 15501.583 | 13612.467 | 11266.684 | 12289.107 | 13167.46 | 1828.53 |
| 0.5 | 13047.082 | 13169.983 | 9508.594 | 10597.55 | 11580.80 | 1819.92 |
| 2 | 11326.279 | 8055.924 | 5952.269 | 8296.324 | 8407.70 | 2212.34 |
| 5 | 6773.314 | 4063.179 | 3914.939 | 3663.777 | 4603.80 | 1455.71 |
| 6 | 2717.981 | 2215.633 | 2155.966 | 1433.272 | 2130.71 | 528.88 |
| 8 | 1577.577 | BLQ | 731.688 | BLQ | 1154.63 | NA |
| 11 | BLQ | BLQ | BLQ | BLQ | NA | NA |
| 14 | BLQ | BLQ | BLQ | BLQ | NA | NA |
| 17 | BLQ | BLQ | BLQ | BLQ | NA | NA |
| 19 | BLQ | BLQ | BLQ | BLQ | NA | NA |
| 22 | BLQ | BLQ | BLQ | BLQ | NA | NA |
| 26 | BLQ | BLQ | BLQ | BLQ | NA | NA |
| 29 | BLQ | BLQ | BLQ | BLQ | NA | NA |
| 36 | BLQ | BLQ | BLQ | BLQ | NA | NA |
| 43 | BLQ | BLQ | BLQ | BLQ | NA | NA |

NA: None/Not applicable;
BLQ: Below the minimum limit of quantitation;
LLOQ = 1 ng/mL

4.3 Pharmacokinetic Parameters

The pharmacokinetic parameters were calculated with non-compartmental model using Phoenix pharmacokinetic software: $AUC_{0-t}$, $AUC_{0-\infty}$, $C_{max}$, $t_{1/2}$, $T_{max}$, C0, Cl, $MRT_{0-\infty}$ and Vss.

The pharmacokinetic parameters of Slit2D2(C386S)-HSA administered intravenously are shown in Table 5.

The ratio of $t_{1/2}$ between male and female in Slit2D2 (C386S)-HSA group was 1.24, the ratio of $C_{max}$ was 1.11, and the ratio of $AUC_{(0-\infty)}$ was 1.41. The main pharmacokinetic parameters ($t_{1/2}$, $C_{max}$ and $AUC_{(0-\infty)}$) of animals of different genders in the group are basically consistent or vary to some extent, and the ratio difference ranges from 1.11 to 1.41.

TABLE 5

Some pharmacokinetic parameters of cynomolgus monkeys after a single intravenous administration of 2 mg/kg of Slit2D2(C386S)-HSA

| Animal No. Gender | $t_{1/2}$ day | $T_{max}$ day | $C_{max}$ ng/mL | C0 ng/mL | $AUC_{(0-t)}$ ng/mL*day | $AUC_{(0-\infty)}$ ng/mL*day | CL mL/day/kg | $MRT_{(0-\infty)}$ day | Vss mL/kg |
|---|---|---|---|---|---|---|---|---|---|
| 101-Male | 2.04 | 0.13 | 16151.83 | 16829.36 | 45588.03 | 50239.09 | 39.81 | 2.84 | 113.09 |
| 102-Male | 2.15 | 0.25 | 13612.47 | 12629.12 | 30270.94 | 37136.49 | 53.86 | 2.81 | 151.45 |
| 103-Female | 1.82 | 0.13 | 13162.76 | 15377.93 | 28598.53 | 30524.24 | 65.52 | 2.58 | 168.88 |
| 104-Female | 1.56 | 0.13 | 13541.87 | 14922.35 | 28034.90 | 31263.33 | 63.97 | 2.10 | 134.46 |
| Mean | 1.89 | 0.16 | 14117.23 | 14939.69 | 33123.10 | 37290.79 | 55.79 | 2.58 | 141.97 |
| SD | 0.26 | 0.06 | 1370.70 | 1741.83 | 8364.03 | 9125.03 | 11.84 | 0.34 | 23.84 |

Example 5

Evaluation of Efficacy on Pulmonary Fibrosis Model

1. Experimental Materials 1.1 Experimental Animals

Experimental animals: SD rats, SPF grade, provided by Beijing Vital River Laboratory Animal Technology Co., Ltd., animal certificate number: 11400700171426.

1.2 Molding Agent

Boremycin hydrochloride for injection, purchased from Nippon Kayaku Co., Ltd.;
Specification: 15 mg/bottle;
Batch number: Y50512;
Production date: Jun. 8, 2015;
Period of validity: until Jun. 7, 2017.

1.3 Solvent

Normal saline: Anhui Double-Crane Pharmaceutical Co., Ltd., product batch number: 160502 8T;
Methyl cellulose: Sigma, Art. No.: M0512-100G, product batch number: 079K0054V;
Tween 80: Aladdin, Art. No.: T104865-500 ml, product batch number: K1519036;
DMSO: NA, Art. No.: NA, product batch number: LE20Q62;
PEG400: Sigma, Art. No.: NA, product batch number: MKBG7718V.

1.4 Preparation of Test and Control Products

Preparation of 0.5% MC/0.2% Tween 80 vehicle: 100 mL of DDW was heated to 80-90° C., and 5 g of methyl cellulose was added thereto and stirred well. The heat source was removed, and about 400 mL of ice DDW was added thereto. The mixture was stirred for 30 minutes in an ice bath, and then the solution was transferred to a 1 L volumetric flask. After returning to room temperature, DDW was added thereto to a final volume of 1 L, and stirred until a clear solution was obtained. 2 ml of Tween 80 was added to 1 L of 0.5% methylcellulose solution, dissolved, and vortexed to obtain a homogeneous solution, which was stored at 4° C. until use.

Preparation of 5.0 mg/ml PFD solution: 1440 mg of PFD powder was weighed and placed in a brown dispensing bottle, and 288 mL of 0.5% MC/0.2% Tween 80 solution was added thereto, and then the resulting mixture was subjected to an ultrasonic water bath to obtain a homogeneous solution, which was allowed to stand for 3 days at 4° C. and then reformulated.

Slit2D2 (C386S)-HSA was diluted with PBS.
Positive control: Pirfenidone, abbreviated as PFD, diluted with PBS.

2. Experimental Methods 2.1 Animal Feeding

Male SD rats, 24, were provided by Beijing Vital River Laboratory Animal Technology Co., Ltd. Animals are kept in a SPF barrier system of an Animal Centre of Nanjing Baijiahui Medicine Research and Development Platform, which followed the international standard temperature, humidity and light control system.

2.2 Model Establishment

Animals were anesthetized by inhaling isoflurane. After confirmation of anesthesia, the animals were sterilized, then the neck skin was cut, the muscles were bluntly separated to expose the trachea, and bleomycin (dosage: 3 mg/kg, volume: 1.0 mL/kg) was directly injected between the tracheal rings. After the operation, the animals were placed in a 37° C. electric blanket to keep warm until the animals were completely awakened. After confirming that they were able to eat and drink freely, the animals were returned to the cage for normal feeding.

2.3 Experimental Grouping

In this experiment, there were four groups, i.e., model group (experimental group-1, n=60), PFD group (experimental group-2, n=6), Slit2D2(C386S)-HSA-1 mg/kg (experimental group-3, n=6), and Slit2D2(C386S)-HSA-5 mg/kg (experimental group-4, n=6). The specific information of the experimental grouping is shown in Table 6.

TABLE 6

| | Experimental grouping | | | | |
|---|---|---|---|---|---|
| Grouping | Number of animals | Modeling | Compound therapy | Administration | Left lung pathology |
| Experimental group-1 | 6 | √ | Vehicle | PO × QD. | 6 |

TABLE 6-continued

Experimental grouping

| Grouping | Number of animals | Modeling | Compound therapy | Administration | Left lung pathology |
|---|---|---|---|---|---|
| Experimental group-2 | 6 | √ | PFD, 50 mg/kg | PO × BID. | 6 |
| Experimental group-3 | 6 | √ | Slit2D2(C386S)-HSA, 1 mg/kg | Iv × Q2D. | 6 |
| Experimental group-4 | 6 | √ | Slit2D2(C386S)-HSA, 5 mg/kg | Iv × Q2D. | 6 |

2.4 Test for Administration

In this experiment, the positive control drug (PFD) was given to rats by gavage twice a day, which was started on the day of modeling, and administered continuously for 14 days. The test compound (Slit2D2(C386S)-HSA) was given intravenously once every other day, which was started on the day of modeling, and a total of seven doses were administered (as shown in table 6).

2.5 Physiological Observation of the Experimental Animals

Physiological observation of the experimental animals: changes in body weight of the animals were measured (body weight was measured once a day before administration); and the death rate of animals during the test period was monitored.

2.6 Test Endpoint

Animals were euthanized 24 hours after the last administration on the 14th day of modeling. After confirming the death of the animals, the left lung was fixed by intrapulmonary infusion of formalin, and the volume and weight of the left lung after perfusion were measured for relevant examination of the pulmonary pathology.

2.7 Pulmonary Pathological Examination

General pathological examination: After the perfusion with an equal amount of formalin in the left lung, the wet weight of left lung after perfusion was weighed/recorded with a micro-balance; and the volume of left lung after perfusion was measured and recorded using a micro-measuring cup.

Figure 7:
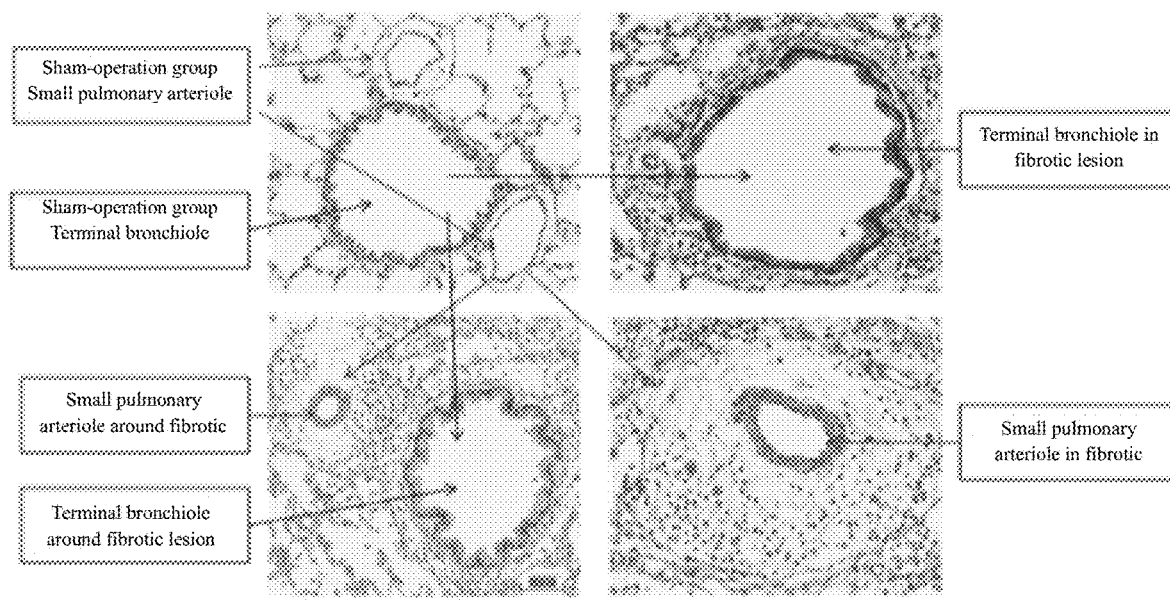
FIG. 7 illustrates a schematic diagram showing the pathological analysis of changes in damage and inflammation of terminal bronchioles and accompanying micropulmonary artery according to Example 5 of the present invention.
Figure 8:
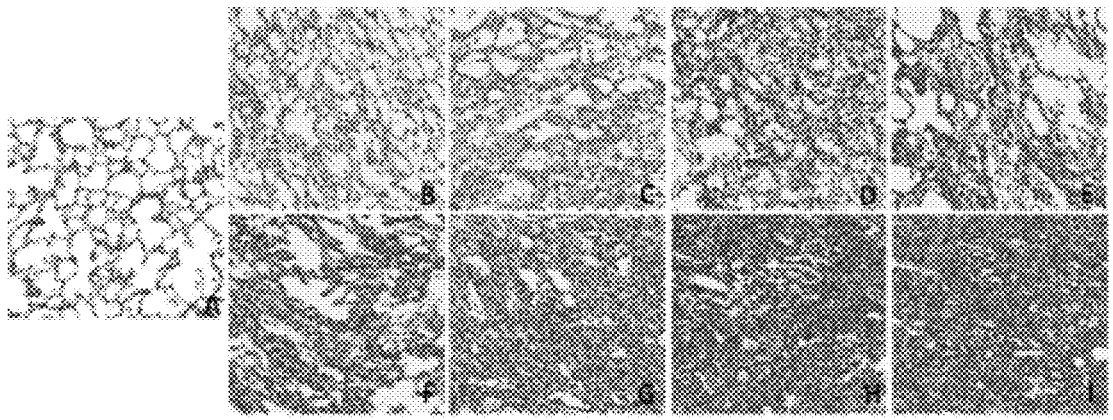
FIG. 8 illustrates a schematic diagram showing the pathological scoring of pulmonary fibrosis according to Example 5 of the present invention (in the schematic diagram, the collagen fibers were stained with toluidine blue).

Pathological examination of lung tissue: The whole lung was dehydrated. Lung paraffin sections were made with paraffin blocks. The HE-stained sections had a thickness of 3 μm, and the Masson Trichrome-stained sections had a thickness of 4 μm. HE staining and Masson Trichrome staining were performed according to pathological staining SOP, and whole section scanning was performed using a Digital Pathscope slice scanner. Pathological analysis and scoring of changes in damage and inflammation of terminal bronchioles and accompanying small pulmonary artery at the periphery of the lesions (as shown in Tables 7 and 8 and FIG. 7) were performed using the HE-stained sections. Lesion area calculation, lesion pathology analysis and scoring were performed with the Masson Trichrome-stained sections (as shown in Table 9 and FIG. 8).

TABLE 7

Pathological evaluation criteria of damage and inflammatory infiltration of the terminal bronchioles

| Score | Damage to the terminal bronchiole wall | Inflammatory cell infiltration of the terminal bronchioles |
|---|---|---|
| 0 | The tissue structure is normal. | The tissue structure is normal and no inflammatory cell infiltration is observed. |
| 1 | The tissue structure is normal, accompanied by wall damage within ½ of the area, manifested as damage, regeneration of bronchial epithelium, edema of wall, degeneration or regeneration of tunica media muscular layer. | Scattered inflammatory cell infiltration can be observed in the tunica externa of wall, which is not focal, and the number of the inflammatory cells is less than 10. |
| 2 | The tissue structure is normal, accompanied by wall damage in more than ½ of the area, manifested as damage, regeneration of bronchial epithelium, edema of wall, degeneration or regeneration of the tunica media muscular layer. | Numerous scattered inflammatory cell infiltrations can be observed in the tunica externa of wall, which are focal, single or multiple, accumulating in less than ½ of the area of the wall. |
| 3 | The tissue structure is normal, accompanied by wall damage in more than ½ of the area, manifested as damage, regeneration of bronchial epithelium, edema of wall, degeneration or regeneration of the tunica media muscular layer, formation of tunica externa granuloma or fibrosis. | Diffuse inflammatory cell infiltration can be observed in tunica externa of wall, accumulating in more than ½ of the area of the wall, or inflammatory cell infiltration can be observed in tunica intima, tunica media. |

TABLE 8

Pathological evaluation criteria of damage and inflammatory infiltration of the small pulmonary arterioles

| Score | Damage to the small pulmonary arterioles | Inflammatory cell infiltration of the small pulmonary arterioles |
|---|---|---|
| 0 | Normal small pulmonary arterioles structure. | Normal small pulmonary arterioles structure. |
| 1 | Exfoliation of the some endothelial cells. | Scattered inflammatory cell infiltration can be observed in the tunica externa of wall, which is not focal, and the number of the inflammatory cells is less than 10. |

TABLE 8-continued

Pathological evaluation criteria of damage and inflammatory infiltration of the small pulmonary arterioles

| Score | Damage to the small pulmonary arterioles | Inflammatory cell infiltration of the small pulmonary arterioles |
|---|---|---|
| 2 | Exfoliation of the endothelial cells, degeneration, hyperplasia or small focal necrosis of the tunica media smooth muscle. | Numerous scattered inflammatory cell infiltrations can be observed in the tunica externa of the wall, which are focal, single or multiple, accumulating in less than ½ of the tunica externa of the wall. |
| 3 | Exfoliation of endothelial cells, degeneration, hyperplasia or small focal necrosis of tunica media smooth muscle, formation of tunica externa granuloma or fibrosis. | Diffuse inflammatory cell infiltration can be observed in the tunica externa of the wall, accumulating in more than ½ of the area of the wall, or inflammatory cell infiltration can be observed in the tunica media. |

TABLE 9

Pathological evaluation criteria of pulmonary fibrosis

| Fibrosis grading | Ashcroft scoring criteria |
|---|---|
| 0 | Alveolar septum: No fibrotic lesions; Lung structure: Normal. |
| 1 | Alveolar septum: Solitary simple fibrotic change (The thickness of the alveolar septum increases, but is less than three times that of a normal lung); Lung structure: Partial enlargement of the alveolar space, small amount of exudate, and no fibrotic material. |
| 2 | Alveolar septum: Clear fibrotic change (The thickness of alveolar septum increases, but is more than three times that of a normal lung) forms into a small nodule, but is not contiguous; Lung structure: Partial enlargement of the alveolar space, small amount of exudate, and no fibrotic material. |
| 3 | Alveolar septum: Uninterrupted fibrosis can be observed in almost all alveolar walls in each high power field (The thickness of alveolar septum increases, but is more than three times that of a normal lung); Lung structure: Partial enlargement of the alveolar space, small amount of exudate, and no fibrotic material. |
| 4 | Alveolar septum: The alveolar septum is still visible; Lung structure: Solitary fibrotic nodules appear in the alveolar space (≤10% of high power field). |

TABLE 9-continued

Pathological evaluation criteria of pulmonary fibrosis

| Fibrosis grading | Ashcroft scoring criteria |
|---|---|
| 5 | Alveolar septum: The alveolar septum is still visible; Lung structure: Fused fibrotic nodules appear in alveolar space (>10% and ≤50% of high power field), and lung tissue structure is severely damaged, but the structure still remains. |
| 6 | Alveolar septum: Visible, but almost nonexistent; Lung structure: Large uninterrupted fibrotic nodules (>50% of high power field), and framework of lung tissue is almost nonexistent. |
| 7 | Alveolar septum: No longer exists; Lung structure: The alveolar space is almost filled with fibrotic material, but there are still less than 5 vacuole-like structures. |
| 8 | Alveolar septum: No longer exists; Lung structure: Under high magnification, alveolar space is filled with the fibrotic tissue. |

2.8 Data Analysis

The mean±sd or mean±sem was calculated using the graphpad prism software, and the significant difference test was performed using t-test, one-way ANOVA and two-way ANOVA test. A significant difference between the two groups was considered at $p<0.05$.

3. Experimental Results 3.1 Basic Physiological Observation of the Animals During Administration All experimental animals showed no obvious physiological and behavioral abnormal changes during the administration.

3.2 Changes in Body Weight of all the Animals During the Experiment

Figure 9:
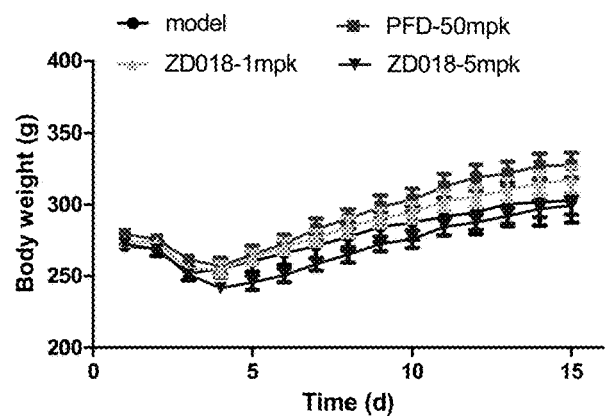
FIG. 9 illustrates a graph showing the results of changes in body weight of animals during the experiment according to Example 5 of the present invention, wherein, ZD018 represents Slit2D2(C386S)-HSA.
Figure 10:
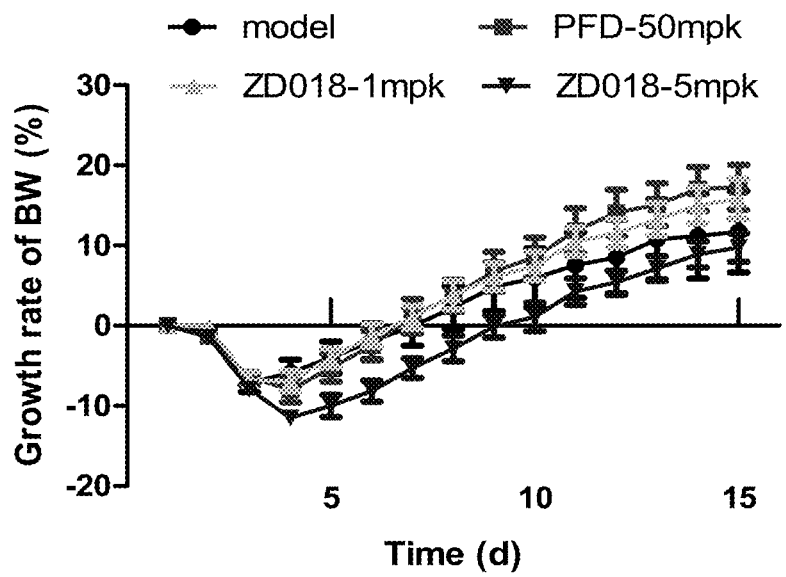
FIG. 10 illustrates a graph showing the results of percentage changes in body weight of animals during the experiment according to Example 5 of the present invention, wherein, ZD018 represents Slit2D2(C386S)-HSA.

During the experiment, the animals in each group had a slight decrease in body weight in a short period of time (5-7 days). The body weight of all the animals gradually increased with the progress of the experiment (the results are shown in Table 10 and FIGS. 9 and 10). The recovery and growth of the body weight of the animals in each administration group were basically consistent with those in the model group. There was no statistically significant difference between the test compound group and the model group, which proved the safety of the drug.

TABLE 10

Changes in body weight of the animals (Mean ± SEM)

| Group | Day 1 | 3 | 5 | 7 | 9 | 11 | 13 |
|---|---|---|---|---|---|---|---|
| Model (QD) | 271.0 ± 3.7 | 251.7 ± 4.6 | 260.3 ± 7.2 | 271.0 ± 8.6 | 284.3 ± 10.6 | 291.7 ± 13.0 | 300.0 ± 15.5 |
| PFD-50mpk (BID) | 279.4 ± 2.3 | 261.8 ± 3.9 | 265.0 ± 6.4 | 282.9 ± 7.4 | 298.4 ± 8.0 | 312.6 ± 8.8 | 321.7 ± 8.3 |
| Slit2D2(C386S)-HSA-1mpk (Q2D) | 273.8 ± 3.1 | 255.2 ± 3.2 | 262.8 ± 4.7 | 276.7 ± 5.4 | 290.7 ± 6.3 | 302.7 ± 6.9 | 310.3 ± 7.8 |
| Slit2D2(C386S)-HSA-5mpk (Q2D) | 272.7 ± 1.8 | 251.8 ± 2.3 | 245.0 ± 5.0 | 258.3 ± 4.4 | 272.5 ± 5.0 | 284.3 ± 5.9 | 292.2 ± 5.6 |

3.3 Results of the General Examination of Lung

Figure 11:
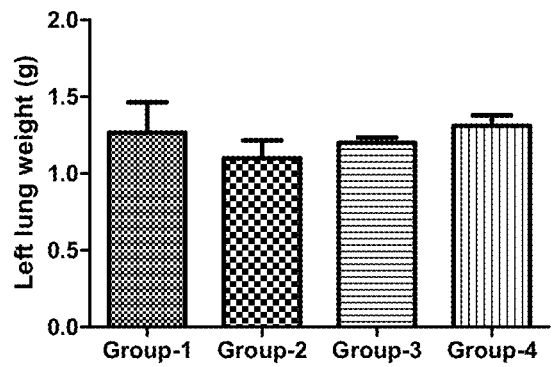
FIG. 11 illustrates a graph showing the results of the changes in wet weight of the left lung of the experimental animals according to Example 5 of the present invention.
Figure 12:
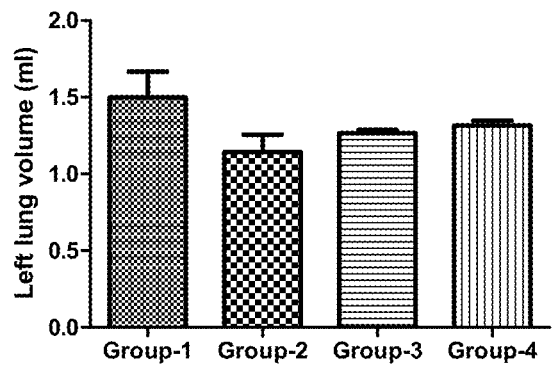
FIG. 12 illustrates a graph showing the results of the changes in volume of the left lung of the experimental animals according to Example 5 of the present invention.
Figure 13:
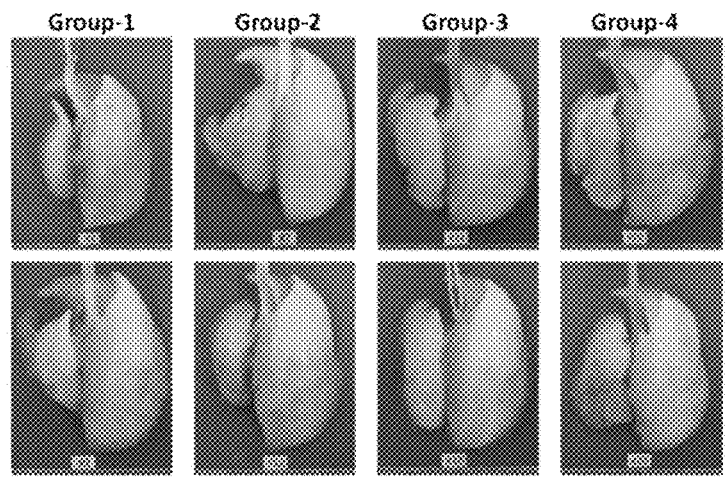
FIG. 13 illustrates a general image of the left lung of experimental animals after perfusion according to Example 5 of the present invention.

The changes in volume and wet weight of the left lung of the animals after perfusion with an equal amount of fixative are shown in Table 11. Compared with the model group, the left lung of the animals in each administration group was reduced in both volume and wet weight, but there was no significant difference. There was no significant difference in the volume and wet weight of the diseased lung tissue in each group. After two weeks of pulmonary fibrosis in the left lung, in each experimental group, the lung volume was reduced and the weight was correspondingly reduced, and there was no significant difference compared with the model group (results are shown in FIGS. 11, 12 and 13).

TABLE 11

Weight and volume of left lung (Mean ± SEM)

| Group | Weight of the left lung (mg) | Volume of the left lung (mm³) |
|---|---|---|
| Model (QD) | 1.27 ± 0.20 | 1.50 ± 0.17 |
| PFD-50mpk (BID) | 1.10 ± 0.12 | 1.14 ± 0.11 |
| Slit2D2(C386S)-HSA-1mpk (BID) | 1.20 ± 0.03 | 1.27 ± 0.02 |
| Slit2D2(C386S)-HSA-5mpk (BID) | 1.31 ± 0.07 | 1.32 ± 0.03 |

3.4 Pathological Evaluation of Injury of the Left Lung

Figure 14:
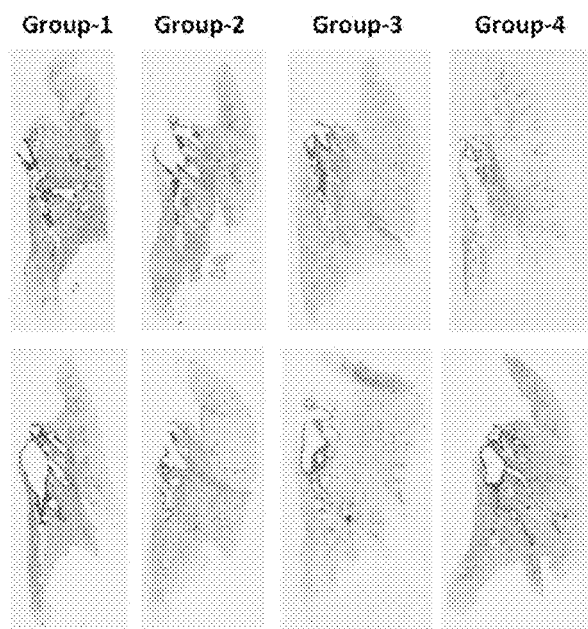
FIG. 14 illustrates HE-stained lung fibrosis lesion area of experimental animals according to Example 5 of the present invention.
Figure 15:
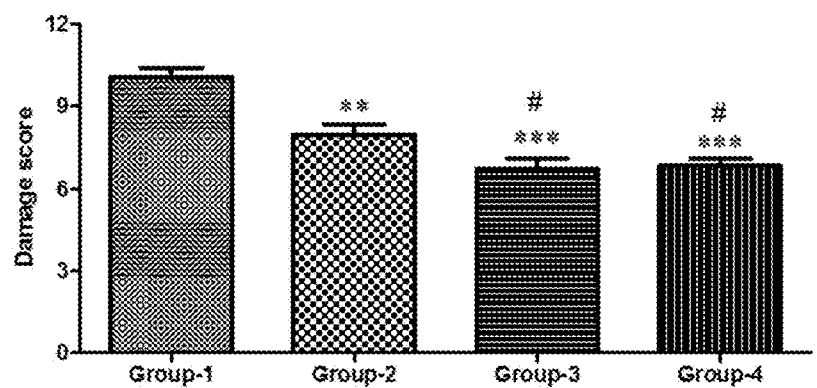
FIG. 15 illustrates the scoring results of damage to bronchioles and small pulmonary arterioles in the pulmonary fibrosis lesions of experimental animals according to Example 5 of the present invention, One-way ANOVA: $p<0.001$ vs. group-1; *$p<0.001$ vs. group-1; T-test: #$p<0.05$ vs. group-2.
Figure 16:
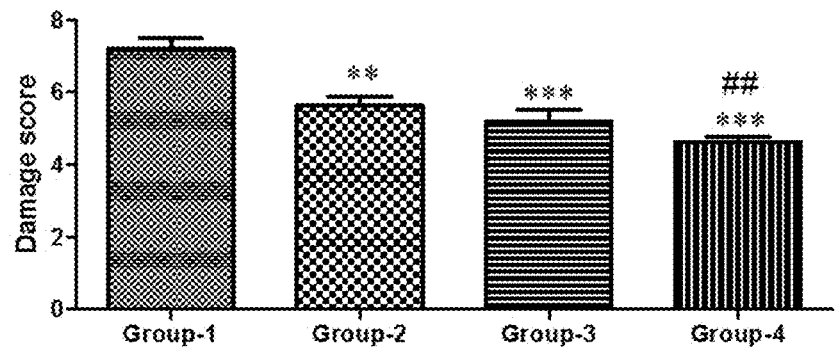
FIG. 16 illustrates the scoring results for damage to bronchioles and small pulmonary arterioles at the periphery of the pulmonary fibrosis lesions of experimental animals according to Example 5 of the present invention, One-way ANOVA: $p<0.01$ vs. group-1; *$p<0.001$ vs. group-1; T-test: #$p<0.05$ vs. group-2.

Histological observation of the diseased lung tissue showed significant lung injury with clear lung tissue boundaries (as shown in FIG. 14), manifested as different degrees of hyperplasia of bronchioles, terminal bronchioles, alveolar duct epithelial cells, goblet cellularity of the some epithelium and even the entire epithelium, variable amounts of mucus tissue visible in the lumen, inflammatory cell infiltration in the wall in different degrees, thickening of some of the wall, smooth muscle hyperplasia and proliferation of granulation tissue in tunica externa of the wall. The alveolar tissue in the lesion was damaged to varying degrees, which was characterized by alveolar epithelial shedding and regeneration, alveolar wall thickening and fibrosis. Inflammatory exudation and inflammatory cell infiltration appeared in the alveolar space. Fibrosis of some alveolar spaces led to loss of the overall alveolar tissue structure. The pharmacodynamic results of the test compounds show that different test compounds exhibit different effects on the damage and inflammatory response of the bronchioles and the accompanying pulmonary arterioles in and around the different fibrotic lesions. Damage and inflammatory pathology were scored for these two regions (as shown in FIGS. 15 and 16). The results show that damage to the terminal bronchioles and small pulmonary arterioles in and around the fibrotic lesions was alleviated to varying degrees by treatment with the test compounds.

3.5 Pathological Evaluation of the Pulmonary Fibrosis

Figure 17:
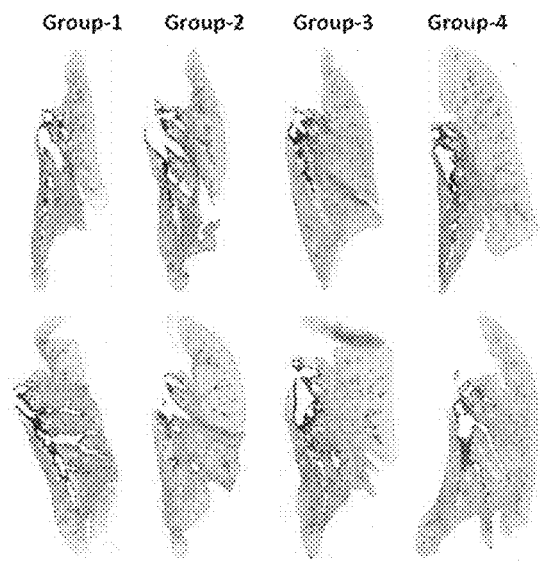
FIG. 17 illustrates the Masson Trichrome-stained pulmonary fibrotic lesion area of experimental animals according to Example 5 of the present invention.
Figure 18:
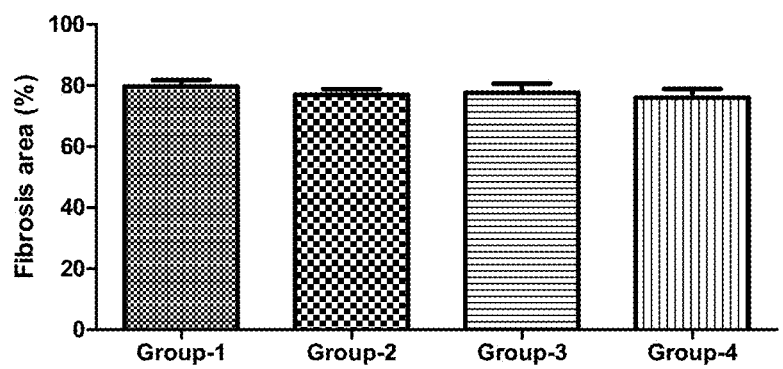
FIG. 18 illustrates the results of the area of pulmonary fibrosis lesion in experimental animals according to Example 5 of the present invention.

Pulmonary histological masson staining clearly showed the uniform fibrotic lesions and the distribution range of the lesions in the left lung (as shown in FIG. 17). The calculated results of the fibrosis area to the left lung area show that the lesion area between the model group and each administration group was basically the same, which suggested the stability and uniformity of the model (as shown in FIG. 18), and the model is reliable for pharmacodynamic evaluation.

Figure 19:
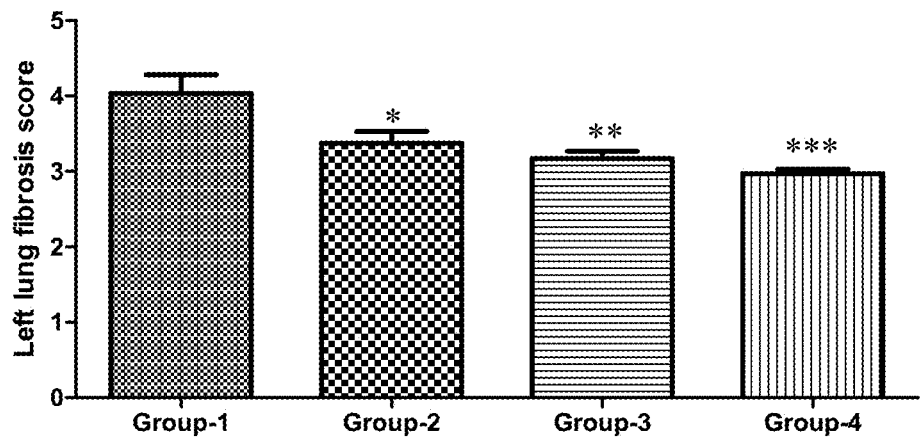
FIG. 19 illustrates the scoring results of pulmonary fibrosis in experimental animals according to Example 5 of the present invention, T-test: *$p<0.05$ vs. group-1; $p<0.01$ vs. group-1; *$p<0.001$ vs. group-1.
Figure 20:
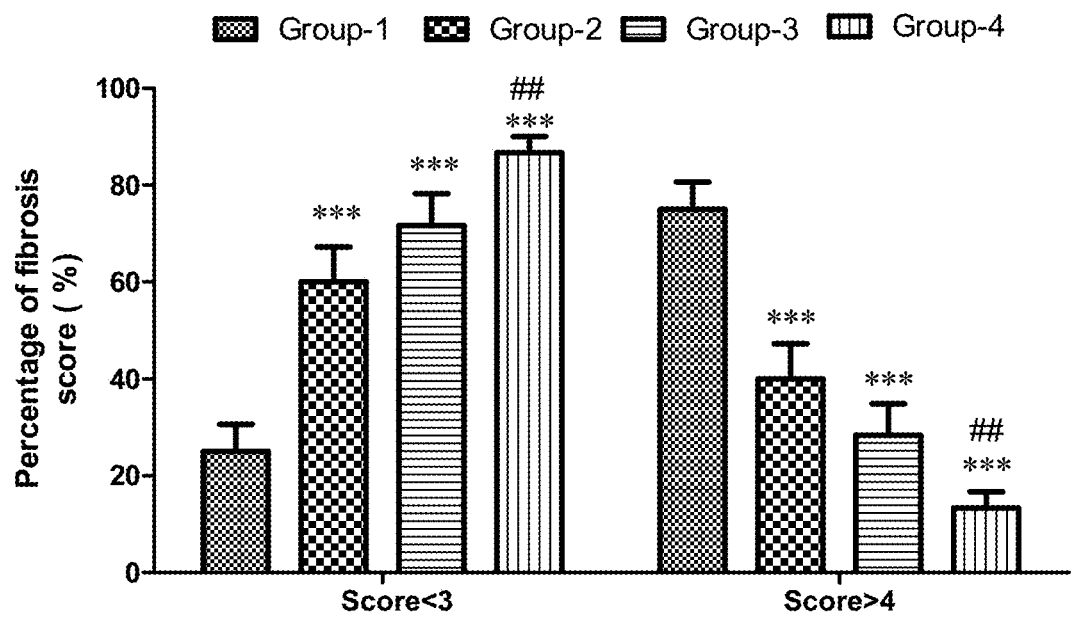
FIG. 20 illustrates the percentage results of scores of pulmonary fibrosis in experimental animals according to Example 5 of the present invention, Two-way ANOVA: ***$p<0.001$ vs. group-1; ##$p<0.01$ vs. group-2.

The pathological changes and degree of the pulmonary fibrosis in left lung were scored using Masson Trichrome staining Histological lesions include alveolar wall structural damage, thickening, inflammatory cell infiltration, collagen fiber deposition; alveolar cavity filled with heterogeneous inflammatory exudate, and fibrotic mass in some alveolar spaces. The normal structure of lung tissue in the severely damaged area completely disappeared and was replaced by fibrosis and inflammatory granuloma tissue. Each test compound group showed different effects in inhibiting fibrosis. Ashcroft scoring results indicated the inhibitory and remission effects of different test compounds on pulmonary fibrosis (as shown in FIG. 19). The percentage of the degree of the pulmonary fibrosis of 3 points or less and 4 points or more in the total fibrosis score was calculated based on 3 points of the pulmonary fibrosis score as the threshold. The results showed that the percentage of lesions less than or equal to 3 points in the model group accounted for about 20% of the entire lesion. However, after drug treatment, the pharmacodynamic response of the various test compounds was observed (as shown in FIG. 20).

4. Conclusion

Direct injection of BLM trachea successfully induced left unilateral pulmonary fibrosis. The area of injury in the left lung of all the animals caused by BLM was uniform, accounting for about 80% of the section of left lung. There were no significant differences between the experimental groups, which suggested that the BLM-induced left lung pulmonary fibrosis model was stable.

Continuous administration of positive control drug (PFD) for 14 days showed significant inhibition on the progression of pulmonary fibrosis.

Intravenous administration of Slit2D2(C386S)-HSA every other day for 2 weeks showed significant inhibition on the progression of pulmonary fibrosis, with a dose-dependent trend. The Slit2D2 (C386S)-HSA 5 mg/kg dose group was superior to the positive compound (PFD) in inhibiting pulmonary fibrosis.

The above is only the preferred embodiment of the present invention, and is not intended to limit the present invention. Any modifications, equivalent substitutions, etc., made within the spirit and scope of the present invention, are intended to be included within the scope of the present invention.

The invention claimed is:

1. A polypeptide or protein comprising or consisting of a D2 domain of a Slit2 protein, the Slit2 protein is derived from human, wherein the cysteine in the D2 domain of the Slit2 protein, corresponding to the 5th cysteine of the Slit2 protein, is located at position 386 of the Slit2 protein and is mutated to a polar amino acid.

2. The polypeptide or protein of claim 1, wherein the polar amino acid is selected from the group consisting of amino acid residues of Ser, Gln, Thr, Asn and Tyr.

3. The polypeptide or protein of claim 2, wherein the polypeptide or protein comprises or consists of the amino acid sequence as shown in SEQ ID NO: 1.

4. A nucleotide encoding the polypeptide or protein of claim 1.

5. The encoding nucleotide of claim 4 having the nucleotide sequence set forth in SEQ ID NO: 2.

6. A fusion protein comprising the polypeptide or protein of claim 1.

7. The fusion protein of claim 6, wherein the polar amino acid is selected from the group consisting of amino acid residues of Ser, Gln, Thr, Asn and Tyr.

8. The fusion protein of claim 6, wherein the polypeptide or protein comprises or consists of the amino acid sequence as shown in SEQ ID NO: 1.

9. The fusion protein of claim 6, wherein the fusion protein further comprises human serum albumin.

10. The fusion protein of claim 9, wherein the fusion protein comprises or consists of the amino acid sequence as shown in SEQ ID NO: 3.

11. A nucleotide encoding the fusion protein of claim 6.

12. The nucleotide of claim 11, wherein the nucleotide comprises or consists of the nucleotide sequence as shown in SEQ ID NO: 4.

13. A method for preventing and/or treating a fibrotic disease or sepsis comprising a step of administering a pharmaceutical composition containing an effective amount of the fusion protein of claim 6.

14. The method of claim 13, wherein the polypeptide or protein comprises or consists of the amino acid sequence as shown in SEQ ID NO: 1.

15. The method of claim 14, wherein the fusion protein further comprises human serum albumin.

16. The method of claim 13, wherein the fusion protein comprises or consists of the amino acid sequence as shown in SEQ ID NO: 3.

17. The method of claim 16, wherein a nucleotide encoding the fusion protein comprises or consists of the nucleotide sequence as shown in SEQ ID NO: 4.

18. The method of claim 13, wherein the fibrotic disease is pulmonary fibrosis, and/or, the sepsis is severe sepsis or septic shock.

* * * * *